United States Patent [19]

Arney

[11] Patent Number: 5,505,702
[45] Date of Patent: Apr. 9, 1996

[54] BALLOON CATHETER FOR DILATATION AND PERFUSION

[75] Inventor: Michelle Arney, Minneapolis, Minn.

[73] Assignee: SCIMED Life Systems, Inc., Maple Grove, Minn.

[21] Appl. No.: 442,081

[22] Filed: May 16, 1995

Related U.S. Application Data

[63] Continuation of Ser. No. 334,631, Nov. 3, 1994, abandoned, which is a continuation of Ser. No. 58,559, May 6, 1993, abandoned, which is a continuation of Ser. No. 866,998, Apr. 9, 1992, abandoned.

[51] Int. Cl.⁶ .................................................. A61M 29/00
[52] U.S. Cl. ........................................ 604/101; 606/194
[58] Field of Search ................... 604/96, 101; 606/191, 606/192, 194

[56] References Cited

U.S. PATENT DOCUMENTS

| | | | |
|---|---|---|---|
| 4,183,102 | 1/1980 | Guiset | 3/1.4 |
| 4,423,725 | 1/1984 | Baran et al. | 128/207.15 |
| 4,581,017 | 4/1986 | Sahota | 604/101 |
| 4,585,000 | 4/1986 | Hershenson | 128/345 |
| 4,661,094 | 4/1987 | Simpson | 604/53 |
| 4,693,243 | 9/1987 | Buras | 128/207.15 |
| 4,762,129 | 8/1988 | Bonzel | 128/344 |
| 4,771,777 | 9/1988 | Horzewski et al. | 128/344 |
| 4,787,388 | 11/1988 | Hofmann . | |
| 4,790,315 | 12/1988 | Mueller, Jr. et al. | 128/344 |
| 4,795,427 | 1/1989 | Helzel | 604/53 |
| 4,820,271 | 4/1989 | Deutsch | 604/99 |
| 4,850,969 | 7/1989 | Jackson | 604/96 |
| 4,877,031 | 10/1989 | Conway et al. | 128/344 |
| 4,878,495 | 11/1989 | Grayzel | 604/101 X |
| 4,892,519 | 2/1990 | Songer et al. | 604/96 |
| 4,901,731 | 2/1990 | Millar | 128/675 |
| 4,909,252 | 3/1990 | Goldberger | 606/194 |
| 4,932,413 | 6/1990 | Shockey et al. | 128/657 |
| 4,944,745 | 7/1990 | Sogard et al. | 606/194 |
| 4,983,167 | 1/1991 | Sahota | 606/194 |
| 5,000,734 | 3/1991 | Boussignac et al. | 604/96 |
| 5,000,743 | 3/1991 | Patel | 606/194 |
| 5,002,531 | 3/1991 | Bonzel | 604/96 |
| 5,071,406 | 12/1991 | Jang | 604/96 |
| 5,078,685 | 1/1992 | Colliver | 604/96 |
| 5,102,416 | 4/1992 | Rock | 606/194 |
| 5,108,370 | 4/1992 | Wallinsky | 604/96 |
| 5,383,856 | 1/1995 | Bersin | 604/101 |
| 5,433,706 | 7/1995 | Abiuso | 604/96 |
| 5,437,638 | 8/1995 | Bowman | 604/101 |
| B1 4,762,129 | 7/1991 | Bonzel | 606/194 |

Primary Examiner—Corrine M. McDermott
Attorney, Agent, or Firm—Peter J. Gafner; Robert E. Atkinson

[57] ABSTRACT

A dilatation balloon catheter capable of creating perfusion passages during balloon inflation is formed by a plurality of cooperating expandable members disposed at a distal end of a catheter shaft, thereby forming a composite balloon. The expandable members are generally side-by-side, and are supported at the distal end of the shaft by at least one support member, which is connected between a distal end of the composite balloon and the catheter shaft. Distal ends of the expandable members are sealed and united within a tubular connector; proximal ends of the expandable members are bonded within and communicate with an inflation lumen at the distal end of the shaft. The outer surfaces of the inflatable members cooperate to dilate the wall of an artery. The outer surfaces of the inflatable members further define two sinuses adjacent to the juxtaposed outer surfaces of the inflatable members, which permit passive perfusion of blood through the composite balloon during a dilatation procedure.

3 Claims, 6 Drawing Sheets

BALLOON CATHETER FOR DILATATION AND PERFUSION

This is a continuation of application Ser. No. 08/334,631, filed Nov. 3, 1994 now abandoned, which is a continuation of application Ser. No. 08/058,559, filed May 6, 1993 now abandoned, which is a continuation of application Ser. No. 07/866,998, filed Apr. 9, 1992 now abandoned.

BACKGROUND OF THE INVENTION

The present invention relates to the field of angioplasty. In particular, the present invention relates to a balloon catheter which is capable of providing prolonged dilatation of a coronary artery without completely blocking blood flow.

Angioplasty has gained wide acceptance as an efficient, effective and alternative method of removing undesirous restrictions caused by tissue growth or lesions on the inner walls of the blood vessels. Such tissue growth or lesions cause a narrowing of the blood vessels called a "stenosis," which severely restricts or limits the flow of blood. In the most widely used form of angioplasty, a dilatation catheter, which has an inflatable balloon at its distal end, is guided through the vascular system. With the aid of fluoroscopy, a physician is able to position an uninflated balloon across the stenosis. The balloon is then inflated by applying fluid pressure through an inflation lumen of the catheter to the balloon. Inflation of the balloon stretches the artery and presses the stenosis-causing lesion into the artery wall to remove the constriction and re-establish acceptable blood flow through the artery.

One disadvantage of many dilatation catheters of the prior art is the complete occlusion of the blood vessel that results while the balloon is inflated. Prolonged complete blockage of a coronary artery poses serious risk of damage to the tissue downstream from the occlusion which is deprived of oxygenated blood. This consequence poses a severe limitation on the length of time the balloon can remain expanded within an artery to effectively remove the stenosis.

Various methods for providing passive perfusion of blood through or past the inflated balloon are found in the following prior art references: Baran et al. U.S. Pat. No. 4,423,725; Sahota U.S. Pat. No. 4,581,017; Hershenson U.S. Pat. No. 4,585,000; Horzewski et al. U.S. Pat. No. 4,771,777; Mueller et al. U.S. Pat. No. 4,790,315; Songer et al. U.S. Pat. No. 4,892,519; Goldberger U.S. Pat. No. 4,909,252; Sogard et al. U.S. Pat. No. 4,944,745; Sahota U.S. Pat. No. 4,983,167; Boussignac et al. U.S. Pat. No. 5,000,734; Patel U.S. Pat. No. 5,000,743; Bonzel U.S. Pat. No. 5,002,531; and Sahota European Patent Application 0 246 998.

The ability to safely and successfully perform dilatation of an occluded artery is enhanced if balloon inflation can be accomplished without any time limitations or oxygen deprivation to tissues downstream from the inflated balloon. There is still a need in the field for a balloon catheter which is capable of performing dilatation of an artery for a time sufficient to remove an occlusion of an artery while permitting oxygenated blood to perfuse past the inflated balloon to tissues downstream from the inflated balloon. Additionally, it would be advantageous for such a balloon catheter to be manufactured with relative ease and minimal cost.

SUMMARY OF THE INVENTION

The present invention is a balloon catheter for dilatation of an artery, which permits oxygenated blood to pass by an inflated balloon during a dilatation procedure to tissues downstream from the inflated balloon. The balloon catheter includes a shaft with a lumen and an inflatable composite balloon disposed at the distal end of the shaft. The composite balloon is formed from a plurality of parallel, generally equal length inflatable members, proximal ends of which are connected to and communicate with the shaft lumen, and distal ends of which are sealed and united. The composite balloon is supported at the distal end of the shaft by at least one support member, which extends within an inflatable member from the distal end of the composite balloon through a proximal end of the composite balloon for a distance within the shaft lumen. The support member is secured within the shaft lumen.

Under fluid pressure, the outer surfaces of the individual inflatable members make contact along at least one contact surface, with the remaining outer surface area of the inflatable members forming a generally cooperative outer balloon surface, which interacts with an artery wall. Sinuses are formed along the length of the composite balloon adjacent to the contact plane by the interaction of the outer surfaces of the inflatable members and the arterial wall. The sinuses permit passive perfusion of blood past the inflated balloon. The composite balloon of the present invention, therefore, is capable of performing dilatation of an artery and remaining inflated within an artery for prolonged lengths of time, which reduces the risk of damage to the tissue downstream from the inflated composite balloon.

DETAILED DESCRIPTION OF THE PREFERRED EMBODIMENTS

Figure 1:
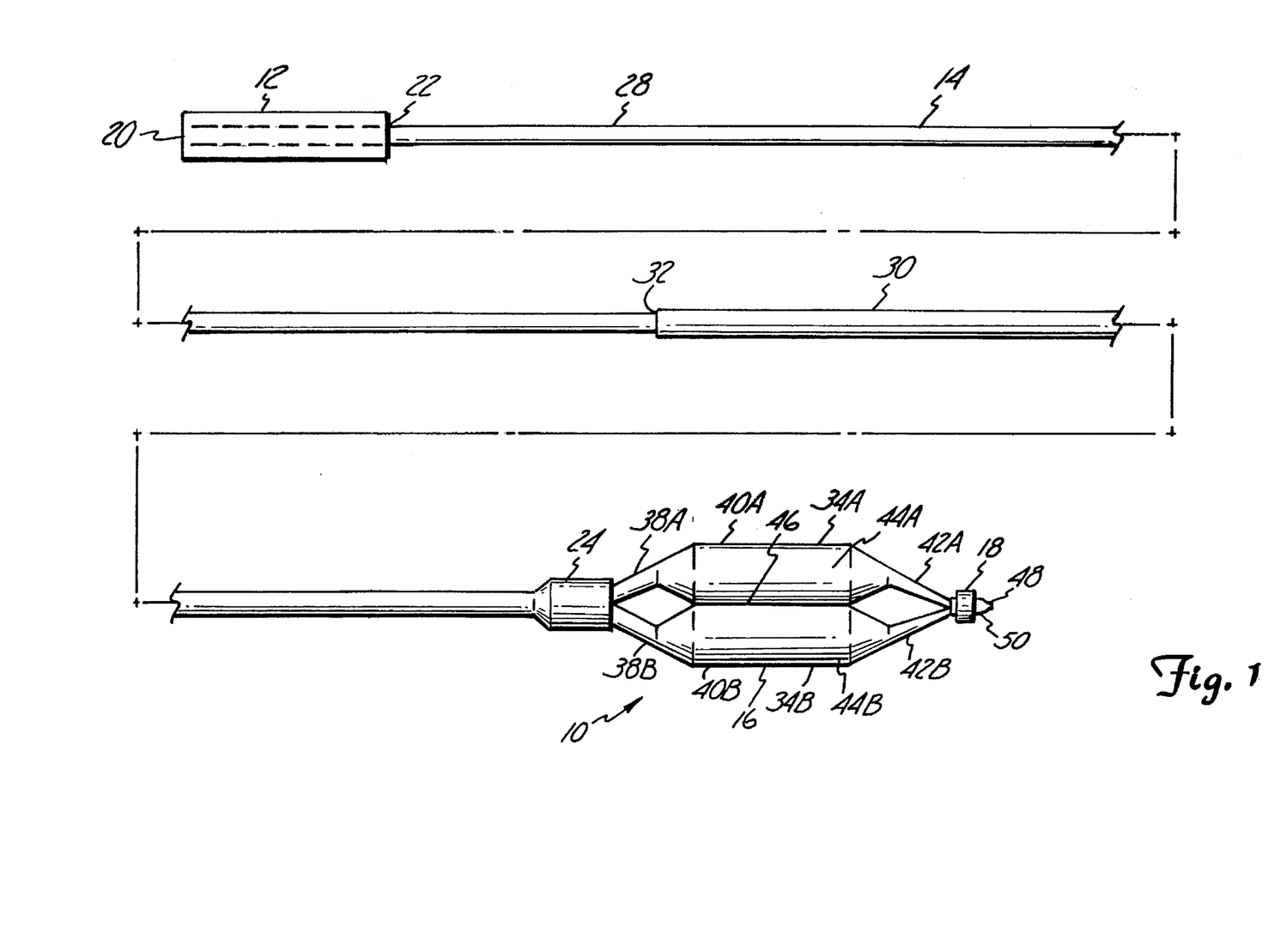
FIG. 1 is a side view of a preferred embodiment of the perfusion dilatation catheter of the present invention.

FIG. 1 shows a side view of perfusion balloon dilatation catheter 10 for performing dilatation of an artery. Catheter 10 generally includes manifold 12, elongated tubular shaft 14, composite balloon 16 and guide wire support tube 18. Manifold 12 is located at the proximal end of catheter 10 and includes inflation port 20, through which inflation fluid is provided to and withdrawn from composite balloon 16.

Elongated tubular shaft 14 is a single lumen tube having its proximal end 22 connected to manifold 12 and its distal end 24 connected to composite balloon 16. Shaft 14 includes lumen 26 (shown in FIGS. 2–3) which extends from proximal end 22 to distal end 24. Lumen 26 of shaft 14 is in fluid communication with inflation port 20 of manifold 12, and also with composite balloon 16. Shaft 14 is comprised of proximal section 28, which is a stainless steel hypotube, and distal section 30, which is made of any one of a number different shaft materials specifically used for angioplasty catheters, such as polyethylene or polyimide. Distal section 30 is connected to proximal section 28 at junction 32. Shaft 14 may also be a single material or multiple materials. In some embodiments, distal section 30 has greater flexibility than proximal section 28. Distal end 24 is flared slightly to accept composite balloon 16.

Composite balloon 16 includes first expandable member 34A and second expandable member 34B. First and second expandable members 34A, 34B are made of tubes of a flexible, inflatable polyolefin copolymer material, such as Surlyn 8527 from Dupont. First and second expandable members 34A, 34B include proximal sections 38A, 38B, intermediate expandable bodies 40A, 40B, and distal sections 42A, 42B, respectively. Each proximal section 38A, 38B has relatively small inner and outer diameters which permits side-by-side insertion of proximal sections 38A, 38B within distal end 24 of shaft 14.

Intermediate expandable bodies 40A, 40B are integral with proximal sections 38A, 38B, respectively. Expandable bodies 40A, 40B are generally parallel, with outer surfaces 44A, 44B of expandable bodies 40A, 40B, respectively, becoming generally contiguous along contact surface 46 when expandable bodies 40A, 40B are inflated. In an inflated state, expandable bodies 40A, 40B each have an expanded inner and outer diameter which is larger than the relatively small inner and outer diameters of proximal sections 38A, 38B.

Distal sections 42A, 42B are integral with expandable bodies 40A, 40B, respectively, with each distal section 42A, 42B having inner and outer diameters which are smaller than the inner and outer diameters of expandable bodies 40A, 40B. Distal sections 42A, 42B converge, and are joined and sealed together by adhering tube 50 over distal sections 42A, 42B at distal end 48. Tube 50 is a relatively short tubular section of an elastic polymer, such as polyurethane, which has an unexpanded inner diameter that is smaller than the combined outer diameter of distal sections 42A, 42B. Tube 50 is stretched so as to increase its inner diameter, thereby permitting insertion of a flexible adhesive, such as urethane 3507 from H. B. Fuller and distal sections 42A, 42B, within tube 50. Tube 50 is then permitted to constrict around distal sections 42A, 42B, which seals and secures together distal sections 42A, 42B.

Positioned over tube 50 at distal end 48 of composite balloon 16 is guide wire support 18. Guide wire support 18 is a relatively short tubular section of a polymer, such as polyethylene, which provides opening 52 (shown in FIG. 2) and permits insertion and free longitudinal movement of a guide wire external to catheter 10.

Figure 2:
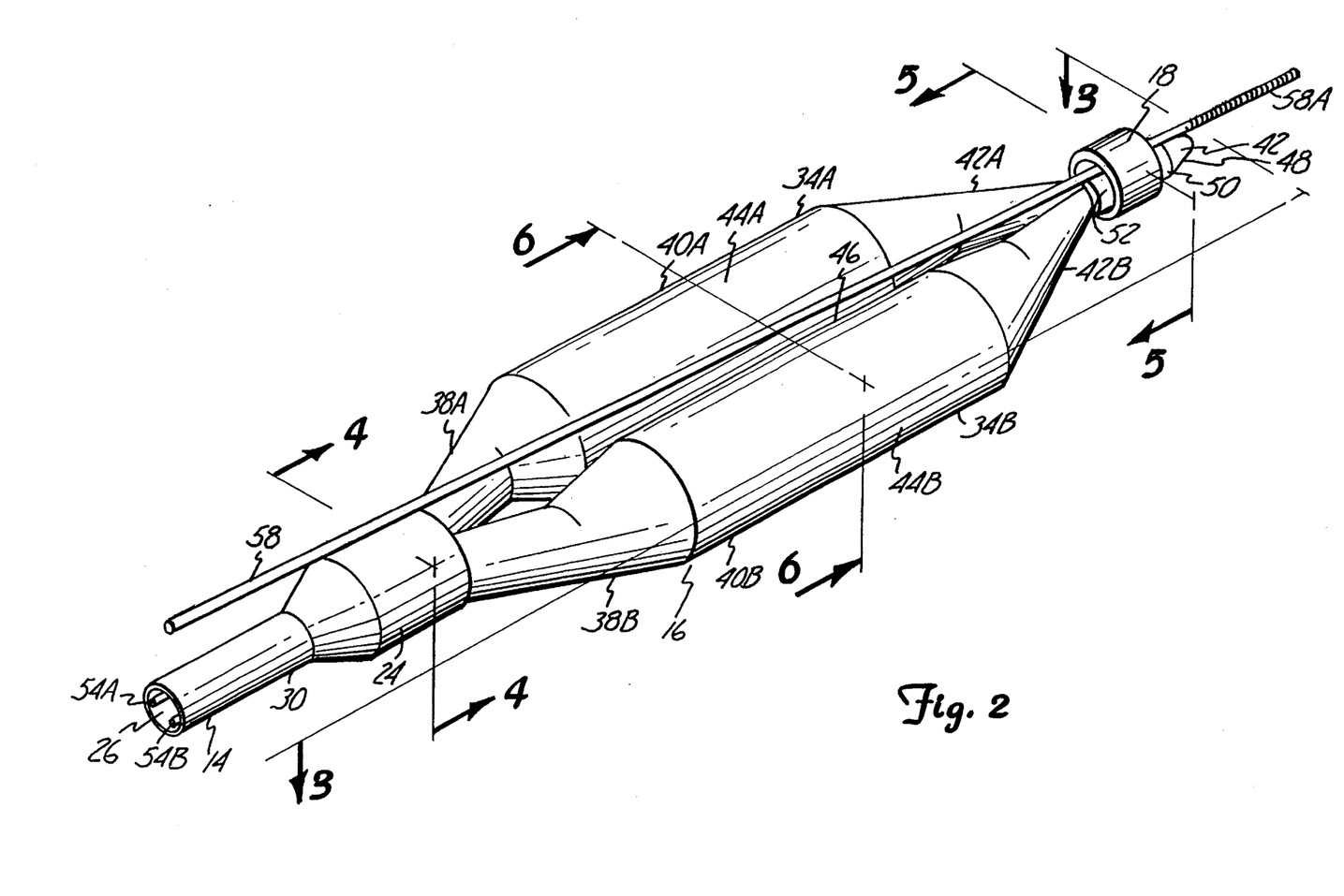
FIG. 2 is an enlarged perspective view of the composite balloon of the perfusion dilatation catheter of FIG. 1 shown with a guide wire.

FIG. 2 is an enlarged perspective view of the distal end of catheter 10. As shown in FIG. 2, composite balloon 16 is supported at distal end 24 of shaft 14 by support members 54A and 54B, which extend from shaft 14 into first and second expandable members 34A, 34B, respectively (shown in FIG. 3). Support members 54A, 54B are made of stainless steel, and provide sufficient rigidity to composite balloon 16 to permit its advancement when catheter 10 is advanced within an artery.

In one embodiment, guide wire support 18 is secured to tube 50 by bond 56 (shown in FIG. 5) such that opening 52 is generally aligned with contact surface 46. Guide wire support 18 has an inner diameter which is larger than an outer diameter of distal end 48. This allows catheter 10 to be advanced over guide wire 58, with guide wire 58 generally positioned between first expandable member 34A and second expandable member 34B adjacent contact surface 46. In an alternative embodiment shown in FIG. 5A, rib 19 bifurcates guide wire support 18 to form openings 53A and 53B. Opening 53B is bonded over tube 50 to secure guide wire support 18 to distal end 48; opening 53A provides a guide wire passage for insertion and free longitudinal movement of a guide wire external to catheter 10. In another alternative embodiment shown in FIG. 5B, guide wire support 18 includes support tube 55, which is bonded within opening 52 by adhesive 57. Support tube 55 provides structural stability to the connection of guide wire support 18 while also providing a passageway for a guide wire.

Guide wire 58 is longer than catheter 10 and generally extends from distal end 48 of composite balloon 16, external to composite balloon 16 and catheter shaft 14, to a point proximal of manifold 12. Guide wire 58 includes distal spring tip 58A, which has sufficient flexibility to facilitate advancement of guide wire 58 through the tortuous curves of an artery, to and across a stenosis of the artery. With guide wire 58 in place within an artery, catheter 10 can be easily advanced over the guide wire 58 to the stenosis. In addition, the location of guide wire 58 external to catheter 10 permits rapid exchange of composite balloon 16 with guide wire 58 remaining in place within the artery across the stenosis.

Figure 3:
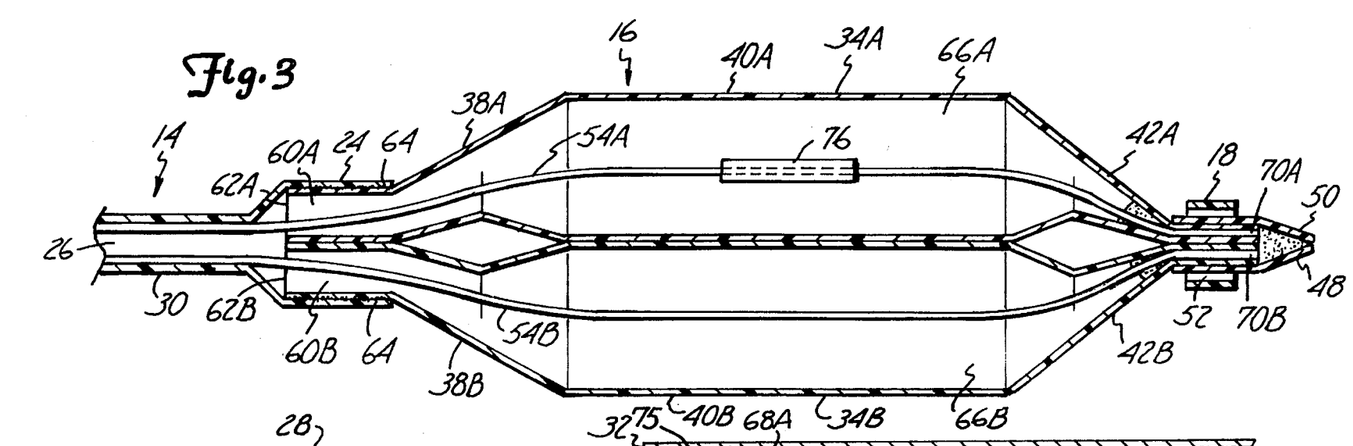
FIG. 3 is a longitudinal sectional view of the composite balloon of FIG. 2 taken along line 3—3.
Figures 3A, 4:
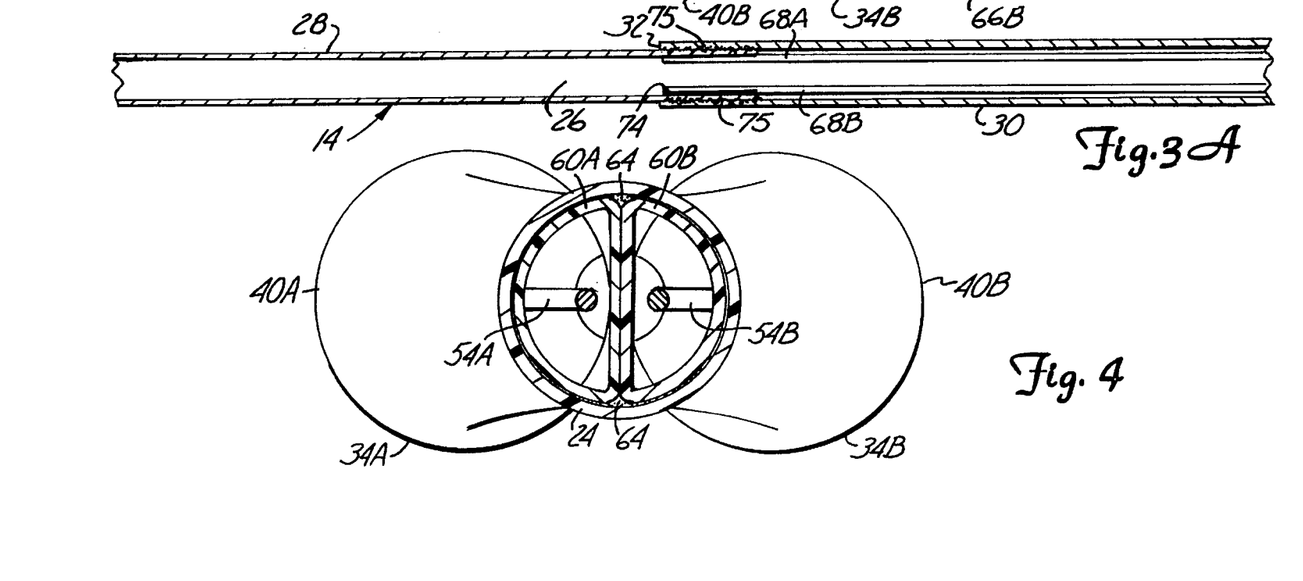
FIG. 3A is a longitudinal sectional view of the shaft of the perfusion dilatation catheter of the present invention.
FIG. 4 is a cross-sectional view of the composite balloon of FIG. 2 taken along line 4—4.

FIG. 3 is a longitudinal sectional view of composite balloon 16 which best shows its bilateral symmetry. First expandable member 34A and second expandable member 34B have generally identical, mirror image contours along the length of composite balloon 16. Proximal ends 60A, 60B of proximal sections 38A, 38B are generally aligned and include openings 62A, 62B, respectively. As shown in FIGS. 3 and 4, proximal ends 60A, 60B of proximal sections 38A, 38B are inserted side-by-side into flared distal end 24 of distal shaft section 30 and sealed therein by bond 64. With distal ends 60A, 60B secured within flared distal end 24, openings 62A, 62B communicate with shaft lumen 26. Openings 62A, 62B further communicate with interiors 66A, 66B of first and second expandable members 34A, 34B.

Figure 5:
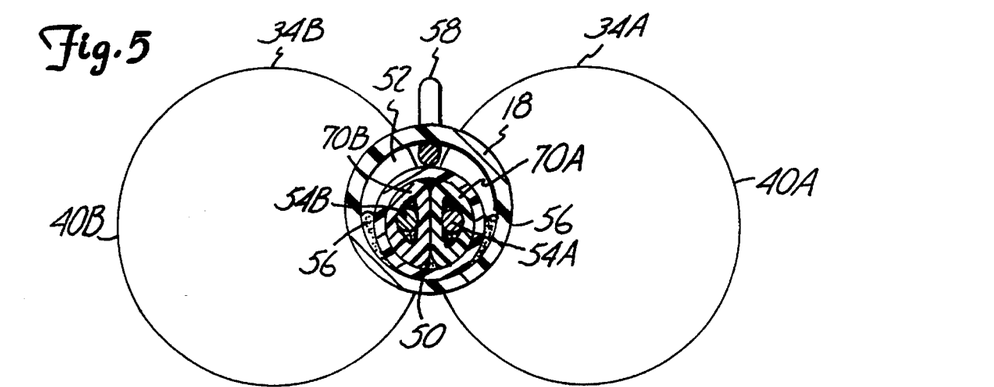
FIG. 5 is a cross-sectional view of the composite balloon of FIG. 2 taken along line 5—5.
Figure 5A:
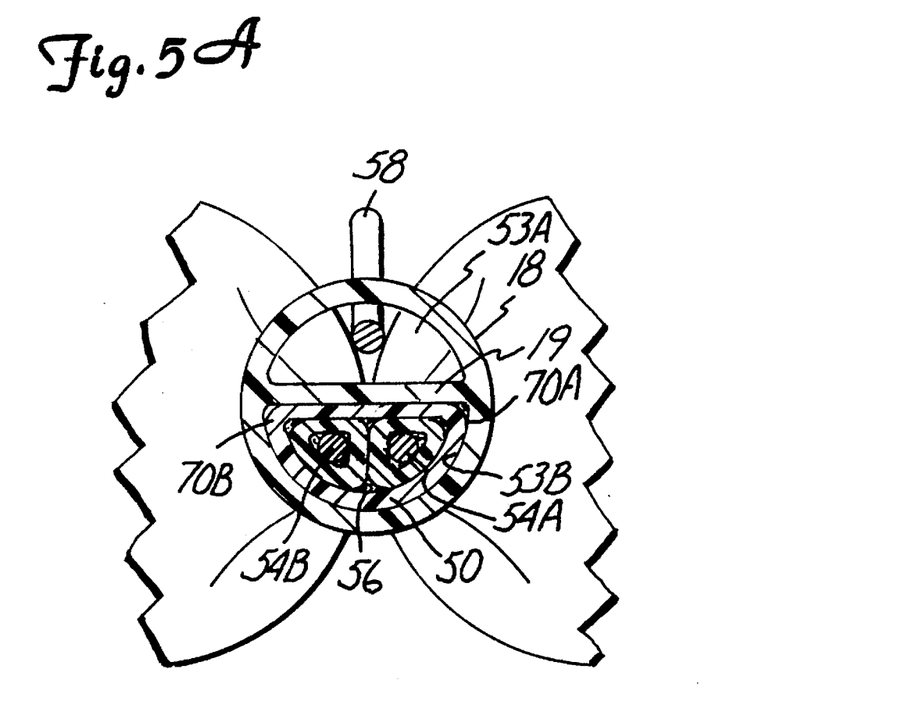
FIG. 5A is a cross-sectional view of a second embodiment of the guide wire support of FIG. 5.
Figure 5B:
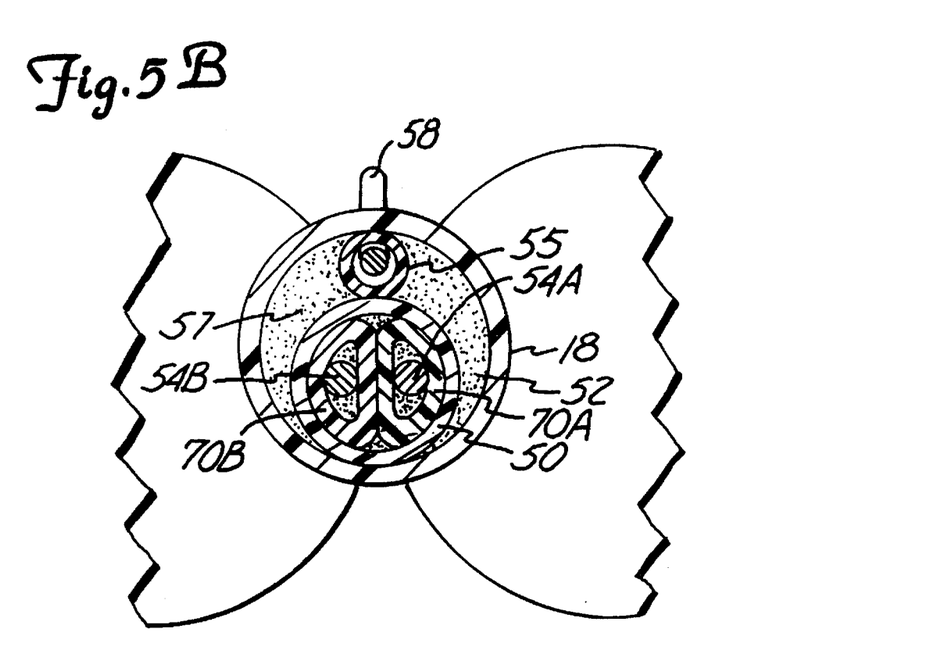
FIG. 5B is a cross-sectional view of a third embodiment of the guide wire support of FIG. 5.

Included within interiors 66A, 66B of first and second expandable members 34A, 34B are support members 54A, 54B. As shown in FIGS. 3 and 5–5B, the distal-most end of support members 54A, 54B are positioned within distal ends 70A, 70B of distal sections 42A, 42B and secured therein by any suitable adhesive material. Distal ends 70A, 70B, which have a combined outer diameter larger than the unexpanded inner diameter of tube 50, are generally aligned, and are joined and sealed together by coating distal ends 70A, 70B with an adhesive material and inserting them within tube 50 while it is expanded. Tube 50 is allowed to constrict around distal ends 70A, 70B to provide a fluid tight seal at distal end 48 of composite balloon 16, thereby permitting expansion of first and second expandable members 34A, 34B when fluid pressure is provided through lumen 26 of shaft 14. Constriction of tube 50 around distal ends 70A, 70B also aids in retaining the distal-most end of support members 54A, 54B within distal ends 70A, 70B at distal end 48 of composite balloon 16.

Positioned within first expandable member 34A on support member 68A is marker band 76. Marker band 76 is made of radiopaque material, as is well known in the art, which permits a physician to monitor the advancement and positioning of composite balloon 16.

As shown in FIGS. 3 and 3A, support members 54A, 54B extend proximally through interior 66A, 66B of first and second expandable members 34A, 34B, out openings 62A, 62B and within lumen 26 to junction 32. The proximal-most ends of support members 54A, 54B are then secured by either bonding or brazing to proximal end 74 of proximal shaft section 28.

As further shown in FIG. 3A, distal shaft section 30 is positioned over distal end 74 of proximal shaft section 28 at junction 32 and secured by bond 75 to effect a fluid-tight connection between proximal shaft section 28 and distal shaft section 30.

Figure 6:
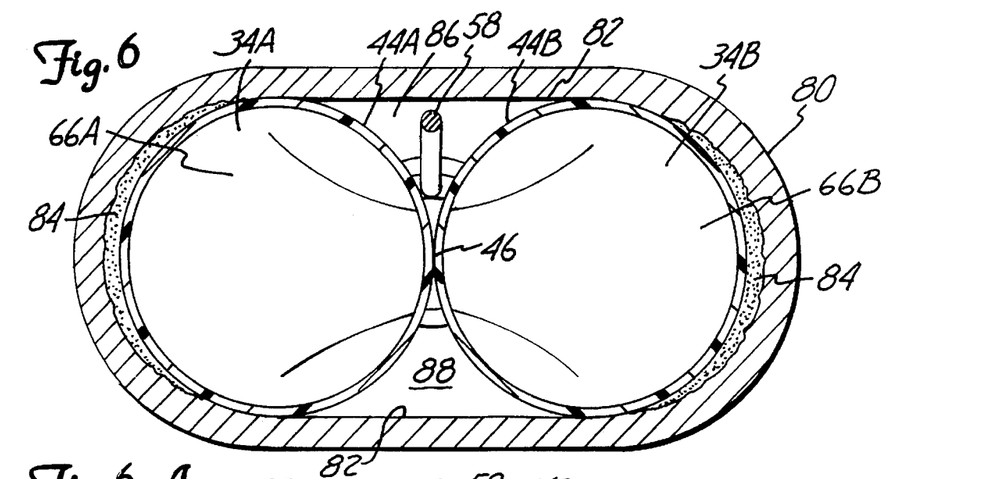
FIG. 6 is a cross-sectional view of the composite balloon of FIG. 2 taken along line 6—6 and shown inflated and positioned within an artery.

FIG. 6 is a cross-sectional view of the composite balloon of FIG. 2 taken along lines 6—6 and shown inflated and positioned within artery 80. Under fluid pressure, expandable members 34A, 34B inflate causing outer surfaces 44A, 44B to make contact at contact surface 46. Expansion of interiors 66A, 66B under fluid pressure cause outer surfaces 44A, 44B to contact and expand artery wall 82 and press lesion 84 into artery wall 82.

The interaction of outer surfaces 44A, 44B adjacent to contact surface 46 also forms sinus 86 and sinus 88, which allow passive perfusion of blood through artery 80 during prolonged inflation of composite balloon 16. In addition to permitting passive perfusion of blood, sinus 86 also accommodates guide wire 58. Guide wire 58 is capable of moving freely through sinus 86 without completely obstructing the passive flow of blood through sinus 86.

Figure 6A:
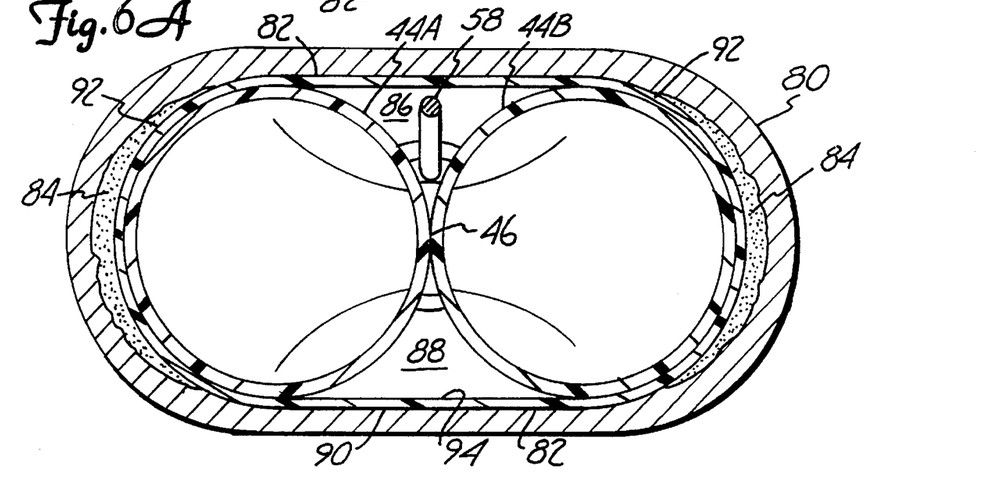
FIG. 6A is a view of the composite balloon of FIG. 6 shown within an artery with a sheath around the composite balloon.

FIG. 6A shows composite balloon 16 of FIG. 6 with sheath 90 surrounding outer surfaces 44A, 44B. Sheath 90 is made of a flexible material which conforms to the general shape of composite balloon 16 when first and second inflatable members 34A, 34B are inflated. Sheath 90 has an outer surface 92 which contacts artery wall 82 of artery 80, and presses lesion 84 into artery wall 82 when composite balloon 16 is inflated. When sheath 90 is used over composite balloon 16, sinus 86 is formed by the interaction of outer surfaces 44A, 44B, contact surface 46 and inner surface 94 of sheath 90. In those embodiments in which it is used, sheath 90 is preferably bonded to exterior surfaces 44A, 44B of composite balloon 16.

Figure 7:
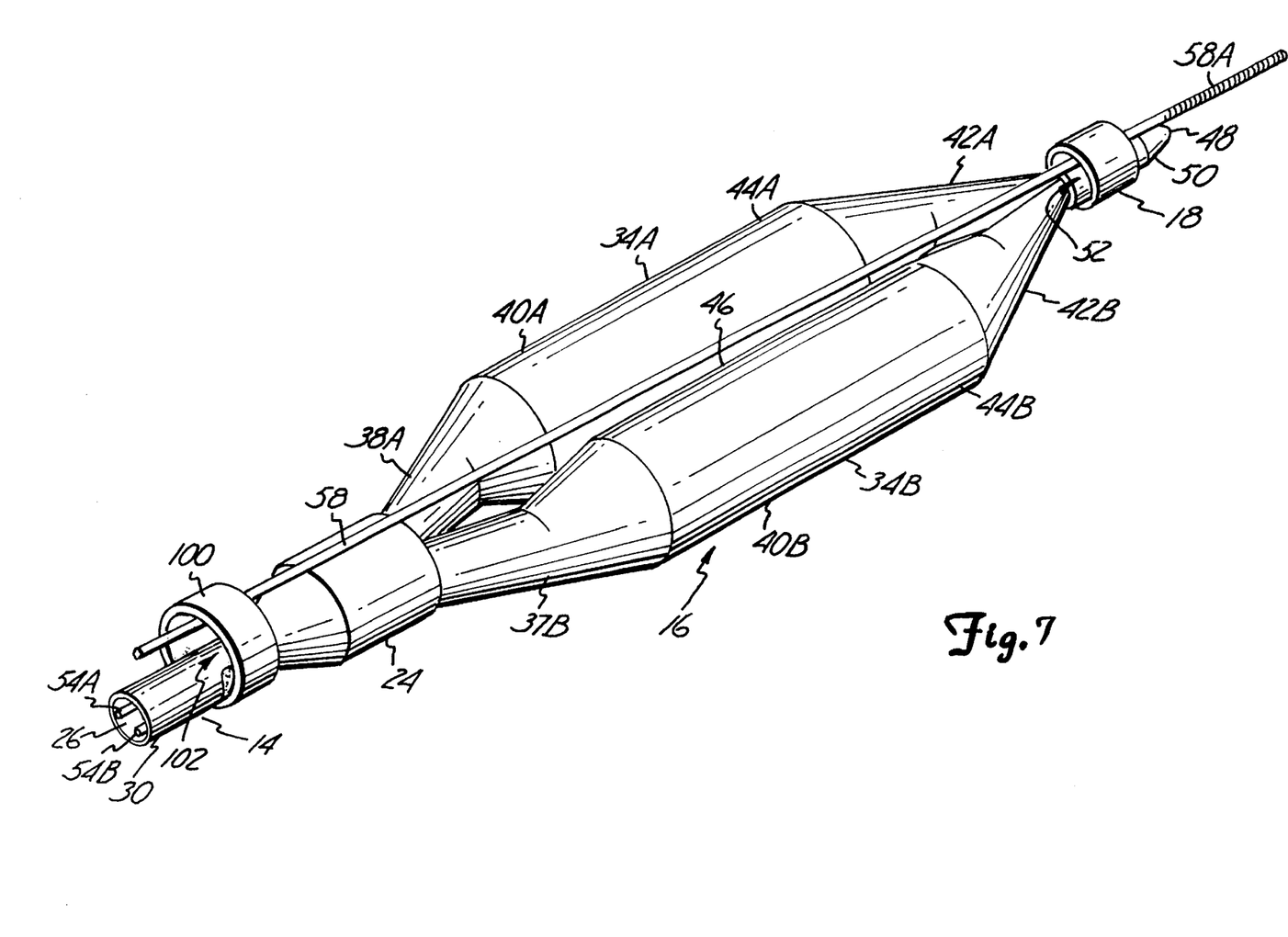
FIG. 7 is an enlarged perspective view of a second embodiment of the composite balloon of the perfusion dilatation catheter of the present invention.

FIG. 7 shows an enlarged prospective view of a second embodiment of composite balloon 16 of the present invention. This second embodiment is similar to the embodiment shown in FIGS. 1–6A with one exception: secondary guide wire support 100 is secured over shaft 14 near flared distal end 24. Secondary guide wire support 100, which is configured similar to guide wire support 18, has an inner diameter which is larger than an outer diameter of distal shaft section 30, thereby creating secondary guide wire passage 102. Secondary guide wire support 100 can also be configured similar to the alternative embodiments shown in FIGS. 5A and 5B. Secondary guide wire support 100 is bonded to distal shaft section 30 and oriented such that secondary guide wire passage 102 is generally aligned with opening 52 of guide wire support 18. The inner diameter of secondary guide wire support 100 is also slightly larger than an outer diameter of flared distal end 24 so as to permit composite balloon 16 to move freely over guide wire 58 when guide wire 58 is inserted through secondary guide wire passage 102 and opening 52. With guide wire 58 inserted in this manner, advancement of composite balloon 16 over guide wire 58 is facilitated by having two spaced apart points of support.

Although the present invention has been described with reference to preferred embodiments, workers skilled in the art will recognize that changes may be made in form and detail without departing from the spirit and scope of the invention.

What is claimed is:

1. An angioplasty catheter for dilatation of a blood vessel, the catheter comprising:

a tubular shaft having a proximal end, a distal end and a lumen extending from the proximal end to the distal end;

a first expandable member disposed at the distal end of the tubular shaft, the first expandable member having a first proximal region with an open proximal end, a first intermediate expandable region and a first distal region with a distal end;

a second expandable member disposed at the distal end of the tubular shaft and juxtaposed to the first expandable member, the second expandable member having a second proximal region with an open proximal end, a second intermediate expandable region and a second distal region with a distal end, the first and second expandable members being sized so that upon inflation the first and second expandable members interact to dilate the blood vessel and create fluid flow passages between outer surfaces of the first and second expandable members and a wall of the blood vessel, wherein the open proximal ends of the first and second proximal regions are generally aligned and communicate with the lumen of the tubular shaft and the distal ends of the first and second distal regions are positioned distally of the distal end of the shaft, and are generally aligned and sealed together;

means connected to the first distal region of the first expandable member and the shaft for supporting the first and second expandable members, and;

at least one guide wire supporting means located external and proximate to the first and second expandable members for guiding the catheter along a guide wire.

2. An angioplasty catheter for dilatation and perfusion of a blood vessel, the catheter comprising:

a tubular shaft having a proximal end, a distal end, and a lumen extending therethrough, for carrying and supplying inflation fluid;

a composite balloon having a first expandable member and a second expandable member, each expandable member having a proximal end and a distal end, the second expandable member juxtaposed to the first expandable member, wherein the proximal ends of the first and second expandable members are generally aligned and open to accept inflation fluid and bonded within the distal end of the tubular shaft and wherein the distal ends of the first and second expandable members are positioned distally of the distal end of the shaft, and are generally aligned and sealed together;

at least one fluid flow passage located between a wall of the blood vessel and outer surfaces of the first and second expandable members when inflated to dilate the blood vessel;

means connected between a distal end of the composite balloon and the shaft for supporting the first and second expandable members and;

a guide wire support attached to the distal ends of the first and second expandable members.

3. A method for widening an obstructed region of a blood vessel comprising the steps of:

providing a catheter having a tubular shaft having a proximal end, a distal end and a lumen extending therethrough for carrying and supplying inflation fluid to a composite balloon, the composite balloon having a first expandable member and a second expandable member, each expandable member having a proximal end and a distal end, the second expandable member juxtaposed to the first expandable member, wherein the proximal ends of the first and second expandable members are generally aligned and open to accept inflation fluid, and wherein the distal ends of the first and second expandable members are positioned distally of the distal end of the shaft and are generally aligned and sealed together, the proximal ends of the first and second expandable members attached to the distal end of the tubular shaft, and means connected between the distal end of the composite balloon and the shaft for supporting the first and second expandable members;

inserting the catheter into the blood vessel such that the composite balloon is aligned with the obstructed region; and inserting inflation fluid into the tubular shaft such that the first and second expandable members expand to dilate the obstructed region and at least one fluid flow passage is located between a wall of the blood vessel and the outer surfaces of the first and second expandable members so that blood can perfuse through the fluid flow passage while the obstructed region is dilated.

* * * * *